United States Patent [19]

Yoshida et al.

[11] Patent Number: 4,640,796

[45] Date of Patent: Feb. 3, 1987

[54] 1,4-DIPYRIMIDINYLBENZENE DERIVATIVE

[75] Inventors: Naoyuki Yoshida, Kamakurashi; Kisei Kitano, Yokohamashi; Yoshito Furukawa, Yokohamashi; Tetsuya Ogawa, Yokohamashi; Shigeru Sugimori, Fujisawashi; Yasuyuki Goto, Yokohamashi; Toyoshiro Isoyama, Yokohamashi; Kazunori Nigorikawa, Yokohamashi, all of Japan

[73] Assignee: Chisso Corporation, Osaka, Japan

[21] Appl. No.: 801,877

[22] Filed: Nov. 26, 1985

[30] Foreign Application Priority Data

Dec. 27, 1984 [JP] Japan ................... 59-279878

[51] Int. Cl.$^4$ ............... C09K 19/34; G02F 1/13; C07D 403/00
[52] U.S. Cl. ............... 252/299.61; 252/299.5; 350/350 R; 350/350 S; 544/295; 544/296
[58] Field of Search ............... 252/299.5, 299.61; 350/350 R, 350 S; 544/295, 296

[56] References Cited

U.S. PATENT DOCUMENTS

| | | | |
|---|---|---|---|
| 3,997,536 | 12/1976 | Boller et al. | 252/299.61 |
| 4,062,798 | 12/1977 | Boller et al. | 252/299.61 |
| 4,389,329 | 6/1983 | Boller et al. | 252/299.61 |
| 4,533,488 | 8/1985 | Fukui et al. | 252/299.61 |
| 4,581,155 | 4/1986 | Goto et al. | 252/299.61 |
| 4,585,575 | 4/1986 | Sugimori et al. | 252/299.61 |

FOREIGN PATENT DOCUMENTS

| | | | |
|---|---|---|---|
| 56501 | 7/1982 | European Pat. Off. | 252/299.61 |
| 0104011 | 3/1984 | European Pat. Off. | 252/299.61 |
| 149238 | 7/1985 | European Pat. Off. | 252/299.61 |
| 160790 | 11/1985 | European Pat. Off. | 252/299.61 |
| 2257588 | 6/1973 | Fed. Rep. of Germany | 252/299.61 |
| 3404116 | 8/1985 | Fed. Rep. of Germany | 252/299.61 |
| 3411571 | 10/1985 | Fed. Rep. of Germany | 252/299.61 |
| 60-25973 | 2/1985 | Japan | 252/299.61 |
| 60-109569 | 6/1985 | Japan | 252/299.61 |
| 60-172971 | 9/1985 | Japan | 252/299.61 |

OTHER PUBLICATIONS

Boller et al., "Synthesis and Mesomorphic Properties of Diphenyl- and Biphenylyl-pyrimidines", *Zeitschrift Fur Naturforschung*, vol. 33b, 1978, pp. 433–438.

*Primary Examiner*—Teddy S. Gron
*Attorney, Agent, or Firm*—Leydig, Voit & Mayer

[57] ABSTRACT

A novel 1,4-dipyrimidinylbenzene derivative which is useful as a component constituting a liquid crystal composition which is superior in properties and also physically and chemically stable, as a material for liquid crystal display elements, and a liquid crystal composition containing the same are provided, which derivative is expressed by the formula

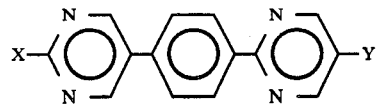

wherein X represents an alkyl group or an alkoxy group each of 1 to 10 carbon atoms, methylthio group or cyano group and Y represents an alkyl group or an alkoxy group each of 1 to 10 carbon atoms.

10 Claims, No Drawings

1,4-DIPYRIMIDINYLBENZENE DERIVATIVE

BACKGROUND OF THE INVENTION

This invention relates to a novel organic compound and more particularly it relates to a novel liquid crystal compound useful as a component of liquid crystal materials.

As well known, liquid crystal compounds have been used for various display devices, making use of specific properties of the compounds in their liquid crystal phases such as dielectric anisotropy, refractive anisotropy, etc. These display devices refer to liquid crystal display elements having applied the electro-optic effect, thermo-optic effect or other optical effects of liquid crystals, and along with advance of electronics, a number of liquid crystal compounds have been used for liquid crystal display elements employing the field effects such as twisted nematic effect, guest-host effect, etc.

For these liquid crystal materials, however, there is no single substance which endures practical use with respect of its various characteristics such as mesomorphic range, operation voltage, response properties, etc.; thus it is the present status that practically, several kinds of liquid crystal compounds have been mixed together or the compounds have been mixed with several kinds of non-liquid crystal compounds to obtain materials which can endure practical use.

SUMMARY OF THE INVENTION

The object of the present invention is to provide a compound which is useful as a component constituting a liquid crystal composition which is superior in practical properties as described above and also physically and chemically stable, as a material for liquid crystal display elements.

The present invention resides in a 1,4-dipyrimidinylbenzene derivative expressed by the formula

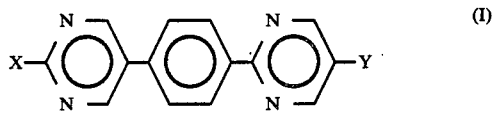

wherein X represents an alkyl group or an alkoxy group each of 1 to 10 carbon atoms, methylthio group or cyano group and Y represents an alkyl group or an alkoxy group each of 1 to 10 carbon atoms, and a liquid crystal composition containing the same.

DESCRIPTION OF PREFERRED EMBODIMENTS

Examples of the compound of the present invention are

2-[4-(2-pentylpyrimidin-5-yl)phenyl]-5-pentylpyrimidine,
2-[4-(2-pentylpyrimidin-5-yl)phenyl]-5-propylpyrimidine,
2-[4-(2-propylpyrimidin-5-yl)phenyl]-5-pentylpyrimidine,
2-[4-(2-propylpyrimidin-5-yl)phenyl]-5-propoxypyrimidine,
2-[4-(2-pentylpyrimidin-5-yl)phenyl]-5-propoxypyrimidine,
2-[4-(2-propoxypyrimidin-5-yl)phenyl]-5-butylpyrimidine,
2-[4-(2-methylthiopyrimidin-5-yl)phenyl]-5-butylpyrimidine,
2-[4-(2-cyanopyrimidin-5-yl)phenyl]-5-butylpyrimidine, etc.

Next, preparation of the compound of the present invention will be illustrated. Compounds of the formula (I) wherein X represents an alkyl group of 1 to 10 carbon atoms or methylthio group and Y represents an alkyl group or an alkoxy group each of 1 to 10 carbon atoms, may be prepared according to the following scheme:

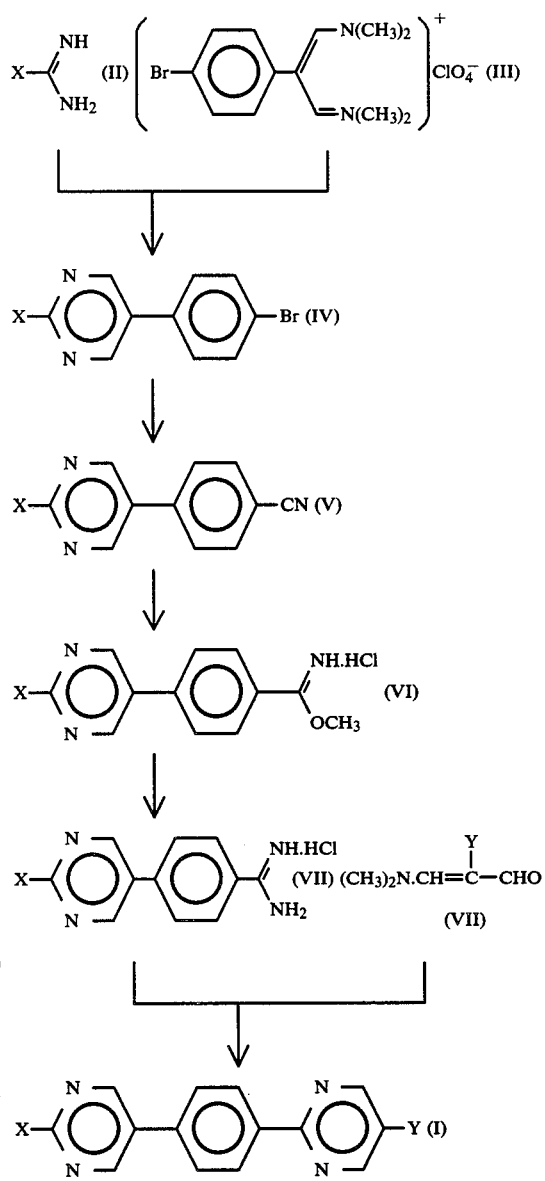

First, an amidine (II) and 1-dimethylamino-3-dimethyliminio-2-(4-bromophenyl)propene-(1) perchlorate (III) are subjected to condensation cyclization reaction in the presence of a suitable basic catalyst such as metal alcoholate, potassium hydroxide, 1,8-diazabicyclo[5.4.0]-7-undecene, triethylamine, etc. to obtain a 2-substituted-5-(4-bromophenyl)pyrimidine (IV).

This compound (IV) is then reacted with cuprous cyanide to obtain a 2-substituted-5-(4-cyanophenyl)- pyrimidine (V). Methanol is added to the compound (V) and hydrogen chloride is passed through the resulting solution to obtain an iminoether hydrochloride (VI). Ammonia gas is passed through an alcohol solution of the iminoether hydrochloride to obtain an amidine hydrochloride (VII).

Next, this amidine hydrochloride (VII) and an α-dimethylamino-β-substituted acrolein (VIII) are subjected to condensation cyclization reaction in pyridine as solvent in the presence of a suitable basic catalyst to obtain the objective 2-[4-(2-substituted pyrimidin-5-yl)phenyl]-5-substituted pyrimidine (I).

Further, the compound of the present invention of the formula (I) wherein X represents cyano group or an alkoxy group of 1 to 10 carbon atoms may be obtained from a 2-[4-(2-methylthiopyrimidin-5-yl)phenyl]-5-substituted pyrimidine (Ia) obtained by the above-mentioned process, through the following process:

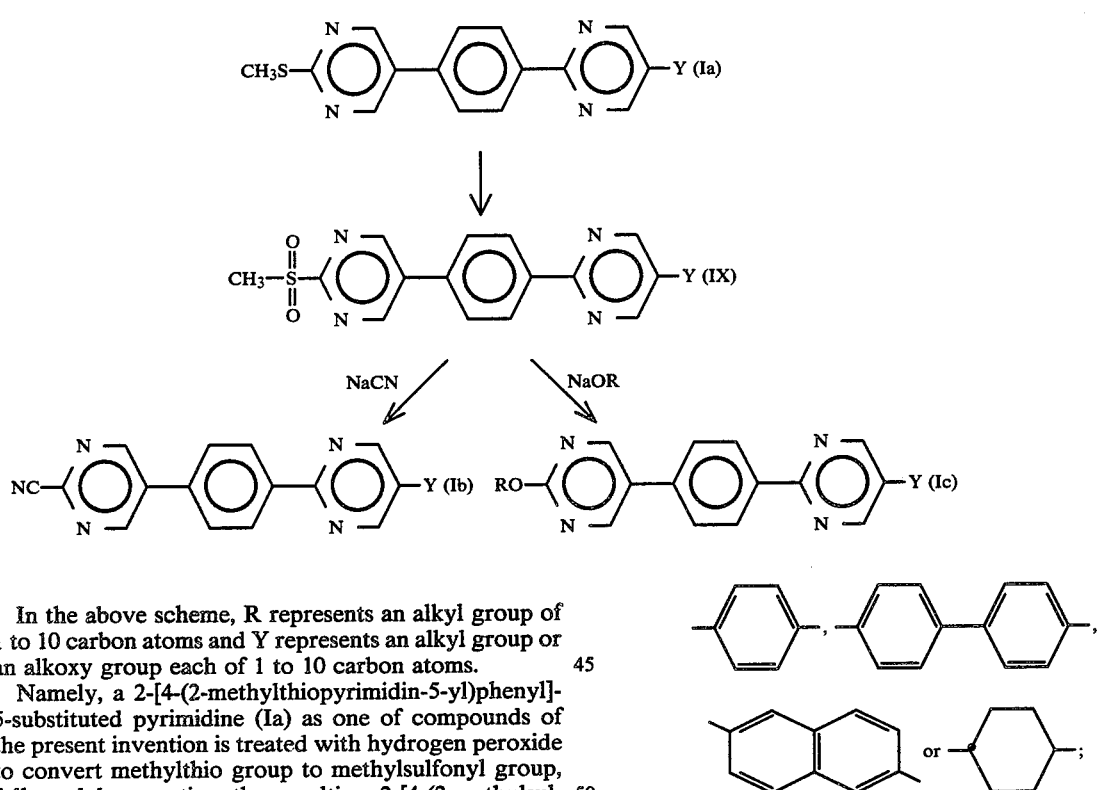

In the above scheme, R represents an alkyl group of 1 to 10 carbon atoms and Y represents an alkyl group or an alkoxy group each of 1 to 10 carbon atoms.

Namely, a 2-[4-(2-methylthiopyrimidin-5-yl)phenyl]-5-substituted pyrimidine (Ia) as one of compounds of the present invention is treated with hydrogen peroxide to convert methylthio group to methylsulfonyl group, followed by reacting the resulting 2-[4-(2-methylsulfonylpyrimidin-5-yl)phenyl]-5-substituted pyrimidine (IX) with sodium cyanide to obtain an objective 2-[4-(2-cyanopyrimidine-5-yl)phenyl]-5-substituted pyrimidine (Ib), or reacting the compound (IX) with a sodium alkoxide to obtain an objective 2-[4-(2-alkoxypyrimidin-5-yl)phenyl]-5-substituted pyrimidine (Ic).

The compound of the present invention has large values of dielectric anisotropy and optical aniostropy in liquid crystal phases and also has a superior stability to heat, light, electricity, air, moisture, etc. which is required for liquid crystal display element materials.

By adding the compound of the present invention as a component of liquid crystal compositions for TN display elements, it is possible to increase the values of the dielectric anisotropy and optical anisotropy of the liquid crystal compositions and broaden the mesomorphic range thereof. Further, by adding the compound of the present invention as a component thereof, it is possible to reduce the driving voltage of TN display elements using the liquid crystal compositions.

The liquid crystal composition of the present invention preferably contains the compound of the present invention of the formula (I) at a level of 1 to 30% by weight, preferably 1 to 15% by weight. If the level of the compounds of the present invention is less than 1% by weight, the contribution to the dielectric anisotropy is small, while if the level exceeds 30% by weight, the viscosity of the composition might increase and thereby reduce the practical properties.

Examples of existing liquid crystal compounds with which the compound of the present invention can be used to give the liquid crystal composition of the present invention are expressed by the following general formulae (i) to (xxxiii):

In these formulae, X represents

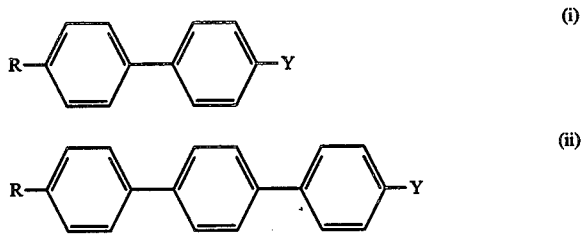

Y represents —CN, —R', halo, or —COO—X—Y', Y' represents —CN, —R' or —OR'; and R and R' each represent an alkyl group.

Furthermore, usable compounds also include those wherein one hydrogen atom in the benzene ring(s) of such compounds is substituted by a halogen atom such as F.

(i)

R—⟨phenyl⟩—⟨phenyl⟩—Y (ii)

R—⟨phenyl⟩—⟨phenyl⟩—⟨phenyl⟩—Y

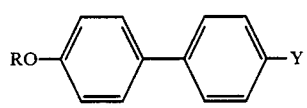 (iii)
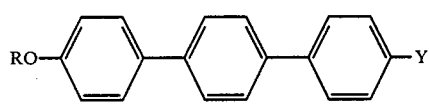 (iv)
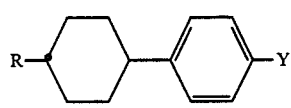 (v)
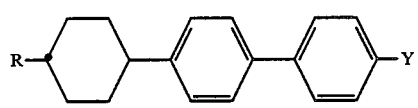 (vi)
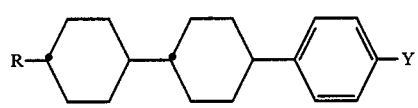 (vii)
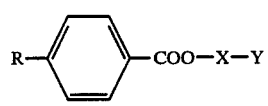 (viii)
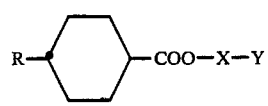 (ix)
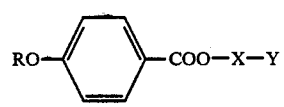 (x)
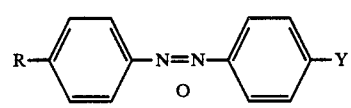 (xi)
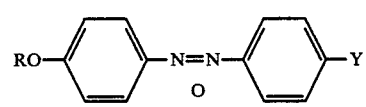 (xii)
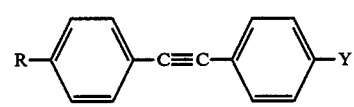 (xiii)
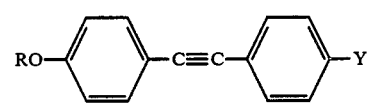 (xiv)
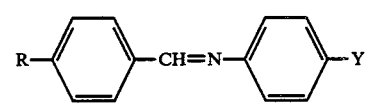 (xv)
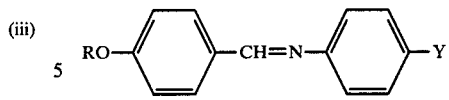 (xvi)
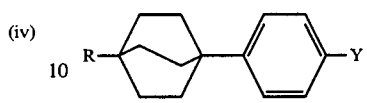 (xvii)
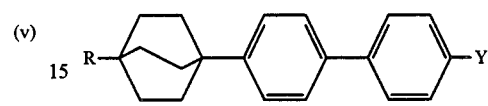 (xviii)
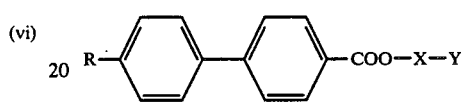 (xix)
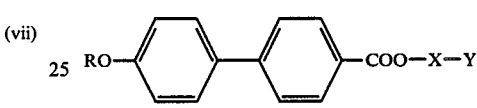 (xx)
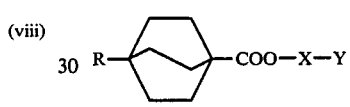 (xxi)
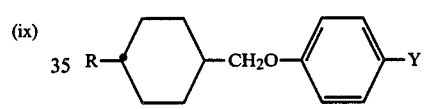 (xxii)
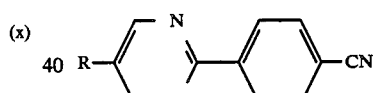 (xxiii)
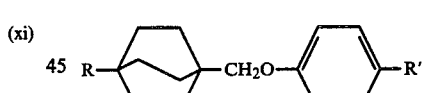 (xxiv)
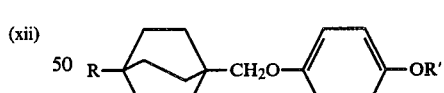 (xxv)
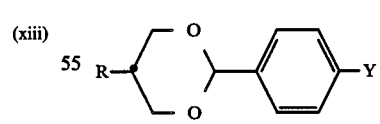 (xxvi)
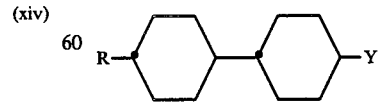 (xxvii)
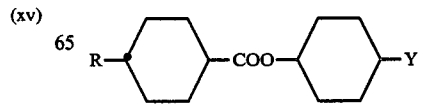 (xxviii)

-continued

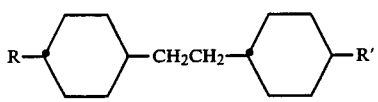 (xxix)

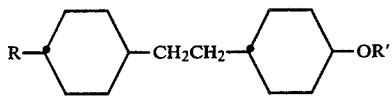 (xxx)

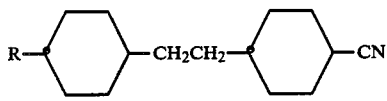 (xxxi)

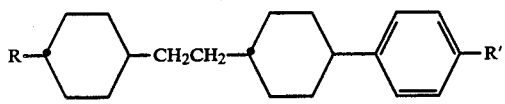 (xxxii)

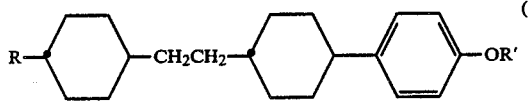 (xxxiii)

The present invention will be described in more detail by way of the following Examples, but it should not be construed to be limited thereto.

EXAMPLE 1

Preparation of 2-[4-(2-pentylpyrimidin-5-yl)phenyl]-5-pentylpyrimidine n-Hexanamidine (57 g, 0.38 mol) and 1-dimethylamino-3-dimethyliminio-2-(4-bromophenyl)propene-(1) perchlorate (40 g, 0.11 mol) were added to pyridine (400 ml) and heated to 90° C., followed by dropwise adding sodium methylate (a solution prepared from sodium (11 g, 0.48 mol) and methanol (300 ml)), further heating the mixture under reflux for 16 hours, then distilling off methanol, adding toluene (500 ml), washing the resulting toluene layer with 2N-hydrochloric acid (400 ml), then with a 2N aqueous solution of NaOH (400 ml) and further with purified water till the washing water became neutral, drying over anhydrous magnesium sulfate, distilling off toluene under reduced pressure to obtain solids, passing a toluene solution of the solids through an alumina column to decolorize the solids, and recrystallizing from methanol to obtain 5-(4-bromophenyl)-2-pentylpyrimidine (26.2 g, yield 76.6%).

This compound (20 g, 0.066 mol) together with cuprous cyanide (7.0 g, 0.039 mol) were added into N-methyl-2-pyrrolidone (80 ml), followed by heating the mixture under reflux for 6 hours, adding toluene (200 ml) when the reaction mixture cooled down to 60° C., further adding a 25% aqueous ammonia (100 ml), agitating the mixture, allowing it to stand still, removing the resulting aqueous layer, thereafter washing the residual layer with water till the washing water became neutral, drying over anhydrous magnesium sulfate, concentrating under reduced pressure to obtain solids, dissolving the solids in toluene, decolorizing the solution of the solids by means of alumina (60 g) and recrystallizing from n-heptane to obtain 5-(4-cyanophenyl)-2-pentylpyrimidine (13.1 g, yield 79.4%).

This cyanide (5.1 g, 0.020 mol) was dissolved in toluene (50 ml), followed by adding methanol (5 ml) to the solution, passing hydrogen chloride gas, driving off excess hydrogen chloride gas, then adding ethanol (100 ml), cooling to 10° C., passing ammonia gas, filtering off deposited white precipitate, and concentrating the residual solution under reduced pressure to obtain 4-(2-pentylpyrimidin-5-yl)benzamidine hydrochloride (6.0 g). This amidine hydrochloride (3 g, 0.01 mol) and α-dimethylamino-β-pentylacrolein (1.7 g, 0.01 mol) were dissolved in pyridine (30 ml) and heated, followed by dropwise adding a methanol solution of sodium methoxide (sodium (0.3 g) and methanol (30 ml)), heating the mixture under reflux for 6 hours, allowing the resulting mixture to cool down, thereafter adding toluene (200 ml) and water (50 ml), separating the resulting toluene layer, then washing it twice with a 3N hydrochloric acid (50 ml), once with a 2N aqueous solution of NaOH (50 ml), further with purified water till the washing water became neutral, drying over anhydrous magnesium sulfate, thereafter concentrating under reduced pressure to obtain solids, passing a toluene solution of the solids through an alumina column and recrystallizing from a mixed solvent of ethyl acetate and toluene to obtain the objective compound (2.0 g, yield 54%). The phase transition points of this compound were as follows: crystalline-smectic (C-S) point, 171.8° C.; smectic-clearing (S-I) point, 213.4° C.

EXAMPLE 2

Preparation of 2-[4-(2-pentylpyrimidin-5-yl)phenyl]-5-propylpyrimidine

Operation was carried out in a similar manner to that of Example 1 to prepare 2-[4-(2-pentylpyrimidin-5-yl)phenyl]-5-propylpyrimidine. This compound had a (C-S) point of 165.8° C. and a (S-I) point of 222.0° C.

EXAMPLE 3

Operation was carried out in a similar manner to that of Example 1 except that n-hexanamidine was replaced by methylisothiourea sulfate, to prepare 2-[4-(2-methylthiopyrimidin-5-yl)phenyl]-5-butylpyrimidine. This compound had a (C-S) point of 215.6° C. and a (S-I) point of 243° C.

EXAMPLE 4

(Use example)

A liquid crystal composition (A) consisting of

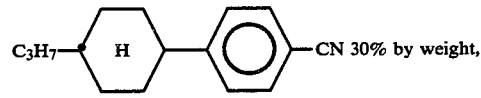 CN 30% by weight,

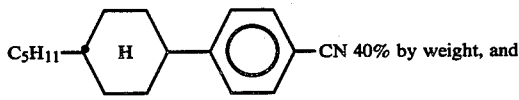 CN 40% by weight, and

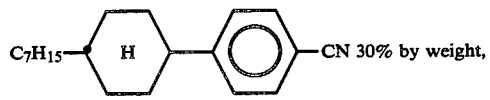 CN 30% by weight, had a nematic-clearing (N-I) point of 52.1° C., a viscosity at 20° C. of 23.4 cp, a dielectric anisotropy value Δε of 11.2 ($\epsilon_\parallel$ =15.9, $\epsilon_\perp$ =4.7), and an optical anisotropy value Δn of 0.119 ($n_e$=1.609, $n_0$=1.490). When this composition was sealed in a TN cell having a cell thickness of 10 mμ, the resulting cell exhibited a threshold voltage of 1.54 V and a saturation voltage of 2.13 V.

When 2-[4-(2-pentylpyrimidin-5-yl)phenyl]-5-pentyl-pyrimidine of Example 1 of the present invention (2 parts by weight) was added to the above liquid crystal composition (A) (98 parts by weight), the N-I point of the resulting liquid crystal composition rose to 54.1° C. and also its Δε and Δn increased to 11.4 and 0.121, respectively. Its viscosity was 28.3 cp at 20° C. When the composition was sealed in the same TN cell, the resulting cell exhibited a threshold voltage of 1.54 V and a saturation voltage of 2.17 V.

EXAMPLE 5

(Use example)

2-[4-(2-Pentylpyrimidin-5-yl)phenyl]-5-propyl-pyrimidine of Example 2 of the present invention (2 parts by weight) was dissolved in the liquid crystal mixture (A) having the same composition as in Example 4 (98 parts by weight). The resulting composition in the form of solution was subjected to the same measurements as in Example 3. As a result the N-I point of the composition rose to 54.1° C. Its Δε and Δn increased to 12.5 and 0.123, respectively. Its viscosity was 24.6 cp. When the composition was sealed in the same TN cell, the threshold voltage and saturation voltage lowered to 1.50 V and 2.06 V, respectively.

We claim:

1. A 1,4-dipyrimidinylbenzene derivative expressed by the formula

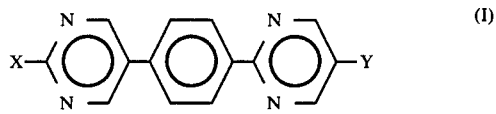

wherein X represents an alkyl group or an alkoxy group each of 1 to 10 carbon atoms, methylthio group or cyano group and Y represents an alkyl group or an alkoxy group each of 1 to 10 carbon atoms.

2. A 2-[4-(2-alkylpyrimidin-5-yl)phenyl]-5-alkyl-pyrimidine according to claim 1.

3. A 2-[4-(2-alkylpyrimidin-5-yl)phenyl]-5-alkoxypyrimidine according to claim 1.

4. A 2-[4-(2-alkoxypyrimidin-5-yl)phenyl]-5-alkyl-pyrimidine according to claim 1.

5. A 2-[4-(2-alkoxypyrimidin-5-yl)phenyl]-5-alkoxypyrimidine according to claim 1.

6. A 2-[4-(2-methylthiopyrimidin-5-yl)phenyl]-5-alkylpyrimidine according to claim 1.

7. A 2-[4-(2-methylthiopyrimidin-5-yl)phenyl]-5-alkoxypyrimidine according to claim 1.

8. A 2-[4-(2-cyanopyrimidin-5-yl)phenyl]-5-alkyl-pyrimidine according to claim 1.

9. A 2-[4-(2-cyanopyrimidin-5-yl)phenyl]-5-alkoxypyrimidine according to claim 1.

10. A liquid crystal composition having at least two components at least one of which is a compound as set forth in claim 1.

* * * * *